United States Patent
Lin et al.

(10) Patent No.: US 6,413,257 B1
(45) Date of Patent: *Jul. 2, 2002

(54) CLAMPING CONNECTOR FOR SPINAL FIXATION SYSTEMS

(75) Inventors: Chih-I Lin, Diamond Bar, CA (US); David Nichols, Memphis, TN (US)

(73) Assignee: Surgical Dynamics, Inc., Norwalk, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/857,137

(22) Filed: May 15, 1997

(51) Int. Cl.[7] .............................................. A61B 17/70

(52) U.S. Cl. .............................. 606/61; 606/72; 606/73

(58) Field of Search .............................. 606/61, 60, 72, 606/73, 54, 59; 623/17

(56) References Cited

U.S. PATENT DOCUMENTS

| 4,269,178 A | * | 5/1981 | Keene |
| 4,641,636 A | * | 2/1987 | Cotrel |
| 4,815,453 A | * | 3/1989 | Cotrel |
| 4,887,596 A | * | 12/1989 | Sherman |
| 4,987,892 A | * | 1/1991 | Krag et al. |
| 5,002,542 A | | 3/1991 | Frigg |
| 5,010,879 A | * | 4/1991 | Moriya et al. |
| 5,074,864 A | * | 12/1991 | Cozad et al. |
| 5,102,412 A | * | 4/1992 | Rogozinski |
| 5,112,332 A | * | 5/1992 | Cozad et al. |
| 5,116,334 A | * | 5/1992 | Cozad et al. |
| 5,122,131 A | * | 6/1992 | Tsou ............................ 606/61 |
| 5,129,900 A | | 7/1992 | Asher et al. |
| 5,176,680 A | | 1/1993 | Vignaud et al. |
| 5,181,917 A | * | 1/1993 | Rogozinski |
| 5,209,752 A | | 5/1993 | Ashman et al. |
| 5,217,497 A | | 6/1993 | Mehdian |
| 5,222,954 A | | 6/1993 | Baker et al. |
| 5,254,118 A | | 10/1993 | Mirkovic |
| 5,257,993 A | * | 11/1993 | Asher et al. |
| 5,261,909 A | | 11/1993 | Sutterlin et al. |
| 5,261,912 A | | 11/1993 | Frigg |
| 5,281,222 A | * | 1/1994 | Allard et al. |
| 5,282,801 A | * | 2/1994 | Sherman |

(List continued on next page.)

FOREIGN PATENT DOCUMENTS

| CA | 2215485 | 9/1996 |
| CA | 2206853 | 12/1997 |
| EP | 0811357 | 8/1997 |
| WO | WO 95/26687 | 10/1995 |

*Primary Examiner*—Michael Buiz
*Assistant Examiner*—David O. Reip

(57) ABSTRACT

The present invention is directed to one piece connector for connecting angularly misaligned implanted pedicle screws to transverse spinal rods in spinal fixation systems. The body portion includes a bore having an inside diameter and a longitudinal axis, with the longitudinal axis of the bore being positioned perpendicular to the longitudinal axis of the leg portion. The leg portion includes a slot placed through a section of the leg portion, along the transverse axis of the leg portion and parallel to the longitudinal axis of the leg portion. The slot intersects the bore of the body portion perpendicular to the longitudinal axis of the bore. The slot allows the one piece connector to be securely clamped around a longitudinal spinal rod when a pedicle screw is implanted at variable distances from the longitudinal spinal rod. The one piece connector allows for angular misalignment of an implanted pedicle screw in relation to a longitudinal spinal rod and the one piece connector, and for the attachment of the one piece connector to both the longitudinal spinal rod and to the implanted pedicle screw with a single locking mechanism when the one piece connector is used in a spinal fixation system.

40 Claims, 3 Drawing Sheets

U.S. PATENT DOCUMENTS

| | | |
|---|---|---|
| 5,282,862 A | 2/1994 | Baker et al. |
| 5,312,404 A * | 5/1994 | Asher et al. |
| 5,330,473 A * | 7/1994 | Howland |
| 5,344,422 A * | 9/1994 | Frigg |
| 5,346,493 A * | 9/1994 | Stahurski et al. |
| 5,368,594 A | 11/1994 | Martin et al. .................. 606/61 |
| 5,380,323 A * | 1/1995 | Howland |
| 5,380,326 A * | 1/1995 | Lin |
| 5,385,583 A | 1/1995 | Cotrel |
| 5,437,669 A | 8/1995 | Yuan et al. |
| 5,437,671 A | 8/1995 | Lozier et al. |
| 5,474,551 A * | 12/1995 | Finn et al. |
| 5,476,462 A * | 12/1995 | Allard et al. |
| 5,478,340 A | 12/1995 | Kluger |
| 5,498,262 A | 3/1996 | Bryan |
| 5,507,746 A | 4/1996 | Lin |
| 5,527,314 A | 6/1996 | Brumfield et al. |
| 5,562,662 A | 10/1996 | Brumfield et al. |
| 5,562,663 A | 10/1996 | Brumfield et al. |
| 5,582,612 A | 12/1996 | Lin |
| 5,591,165 A | 1/1997 | Jackson |
| 5,609,592 A | 3/1997 | Brumfield et al. |
| 5,611,800 A | 3/1997 | Davis et al. |
| 5,613,968 A | 3/1997 | Lin |
| 5,630,817 A | 5/1997 | Rokegem et al. |
| 5,634,925 A | 6/1997 | Urbanski |

* cited by examiner

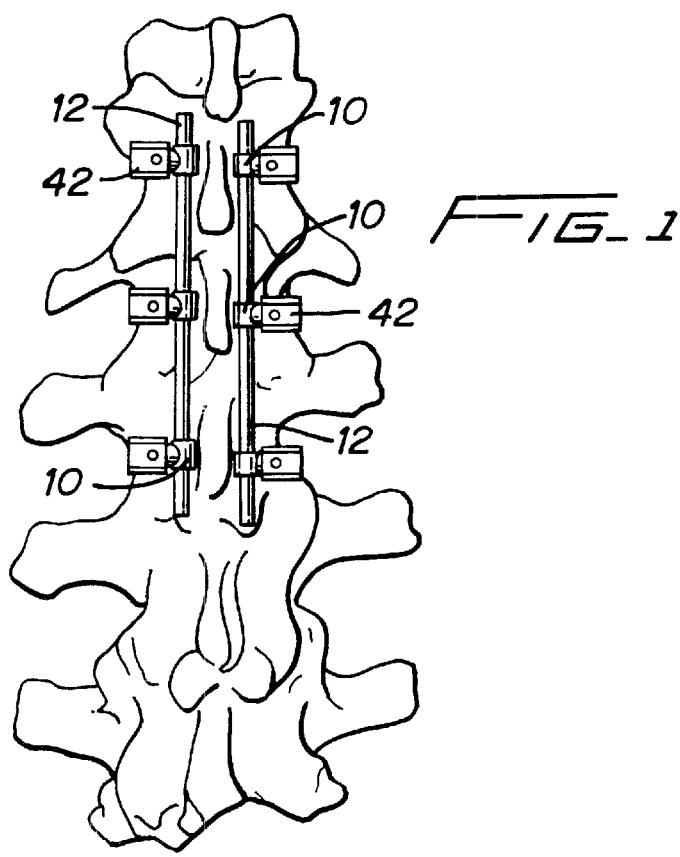
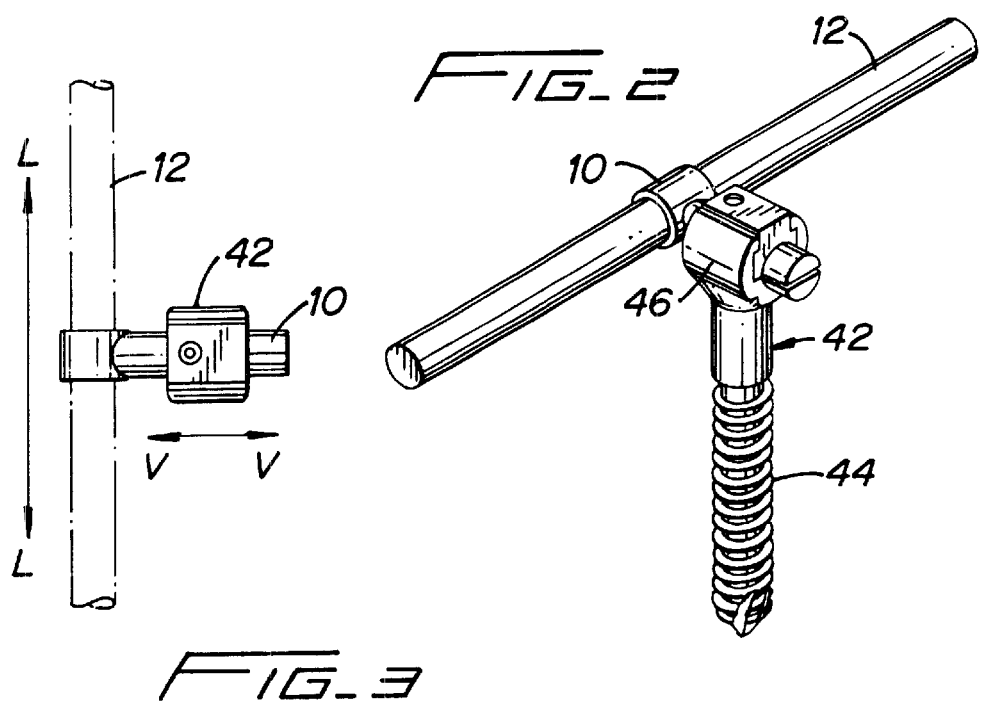

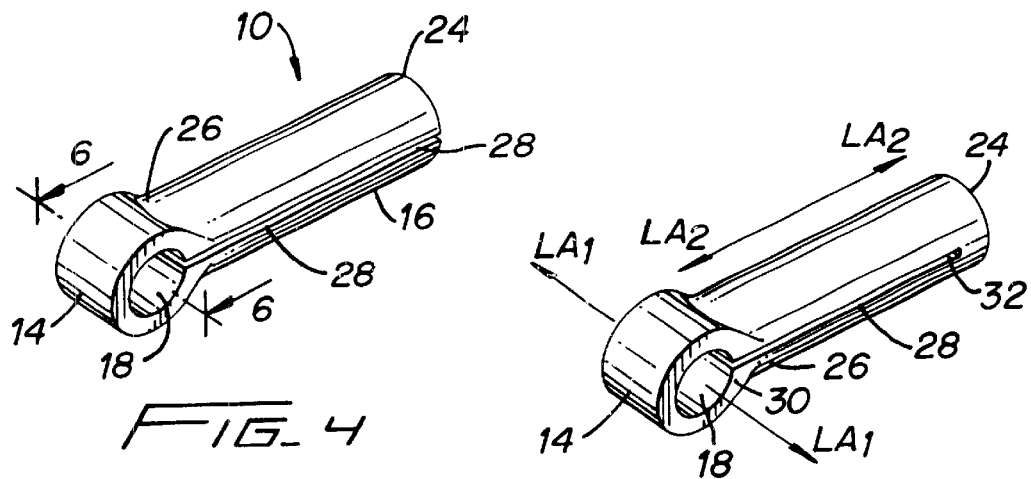
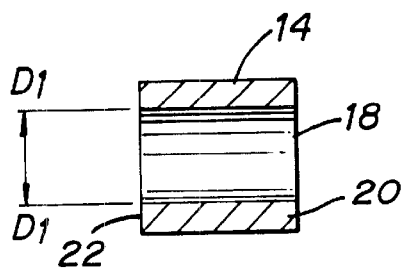
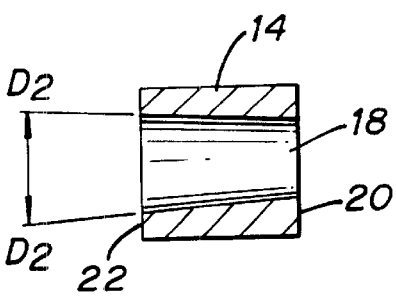
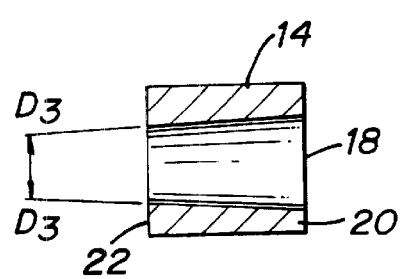
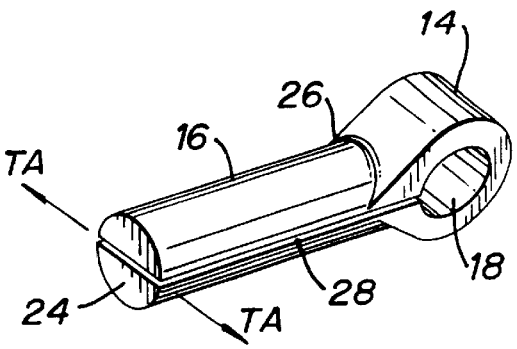
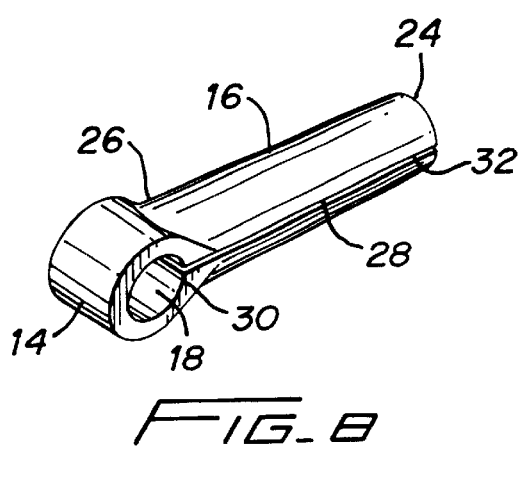

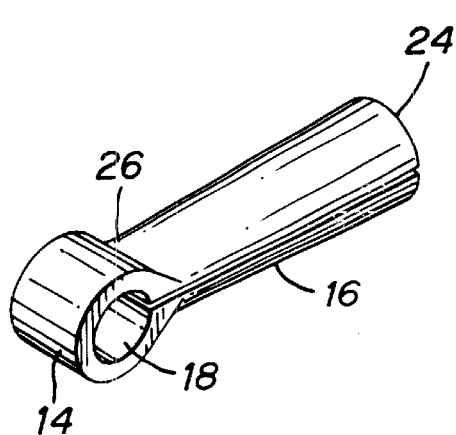
FIG_9
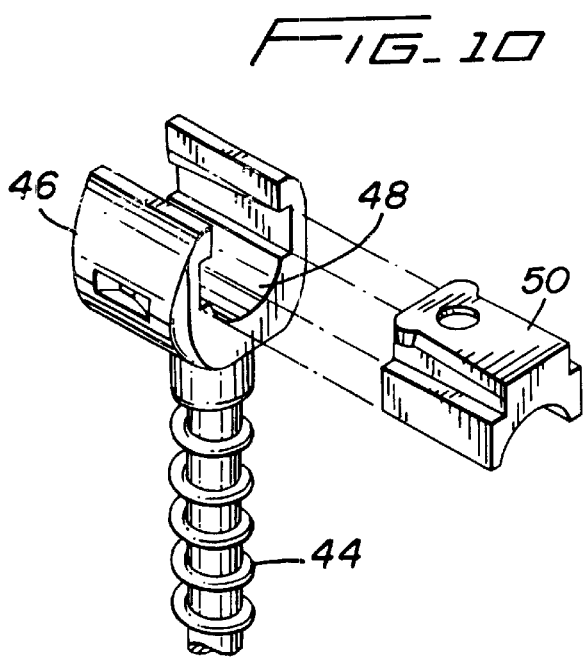
FIG_10
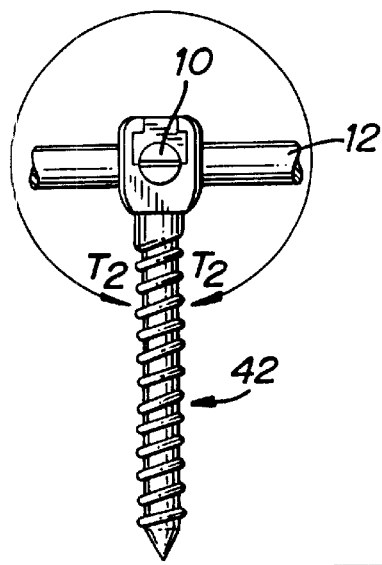
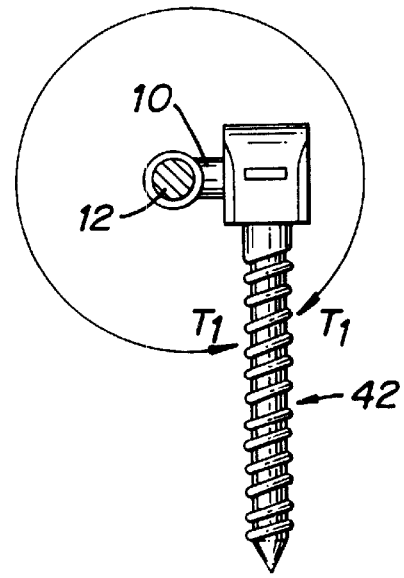
FIG_11
FIG_12

CLAMPING CONNECTOR FOR SPINAL FIXATION SYSTEMS

BACKGROUND OF THE INVENTION

1. Field of the Invention

The present invention relates to spinal fixation systems for use in the treatment of spinal deformities and more particularly to a clamping connector for attaching angularly misaligned pedicle screws to transverse spinal rods in spinal fixation systems.

2. Description of the Prior Art

Surgeons treat spinal disorders with spinal fusion augmented with longitudinal spinal rods connected to the spine with lamina hooks or pedicle screws. Such "rod assemblies" generally comprise one or two spinal rods and a plurality of screws inserted through the pedicles and into their respective vertebral bodies. The screws are provided with coupling elements, for coupling the elongate rod to the screws. The rods extends along the longitudinal axis of the spine, coupling to the plurality of screws via their coupling elements. The aligning influence of the rod forces the spine to which it is affixed, to conform to a more proper shape.

Due to anatomical variations, pedicle screws may not properly align with the longitudinal spinal rods. In order to eliminate the need for lateral rod bending, a device is required to connect the rod to the screws in such a way as to compensate for lateral deviation of the spinal rods.

The art contains a variety of attempts at providing instrumentation that permits a range freedom with respect to angulation of the screw and the coupling element. These teachings, however, have generally been complex, and unreliable with respect to durability. The considerable drawback associated with the prior art systems include complexity, difficulty properly positioning the rod and the coupling elements, and the tedious manipulation of many small parts associated with the complex spinal fixation devices.

Various connector designs exists to accommodate screws offset from the rod, these include the Smith & Nephew Rogozinski (U.S. Pat. 5,102,412) and Finn Systems (U.S. Pat. No. 5,474,551), the Synthes Universal System, and the Zimmer Modulok System (now the Wrightlok System from Wright Medical).

Each of these systems require two locldng mechanisms for the connector—one to link the pedicle screw to the connector and another to link the connector to the rod. Some of these devices provide variable lateral adjustment while other provide only a fixed distance of offset. The Sofmor Danek TSRH System (U.S. Pat. No. 5,282,801) provides a means to offset a screw from the rod with a single set screw yet the lateral distances are fixed.

Other types of screws, hooks and clamps have been used for attaching corrective spinal instrumentation to selected portions of the patient's spine. Examples of pedicle screws and other types of attachments are shown in U.S. Pat. Nos. 5,562,662, 5,498,262, 5,312,404, 5,209,752 and 5,002,542.

However, many current bolt to rod connectors constrain the bolt or screw to a predetermined angle in relation to the connector when the assembly is tightened. Tightening the bolt or screw to the connector forces the bolt or screw into a position perpendicular to the connector, creating stresses on the connector and on the bone as the bolt or screw is forced into the perpendicular position.

When spinal rod system are implanted in the sacral region of the spine, the bone screws need to allow for the variability in angulation found between the sacral and lumbar vertebrae. The bone screws also need to be able to pivot in the medial/lateral plane as well as have the ability to pivot and lock in the cephalad/caudal plane while maintaining the proper alignment between an implanted bone screw, a coupler and a rod of a spinal fixation system.

Accordingly, it is a principal object of the present invention to provide a spinal rod linkage apparatus for connecting two or more vertebral bodies in a lateral direction whereby healing of a bone graft between the vertebral bodies is enhanced.

It is another object of the present invention to provide a connector that compensates for angular misalignment, in the transverse plane between both the implanted bolt or screw and the spinal rod, and the bolt or screw and the connector in order to reduce stress on the bolt or screw when it is firmly fastened to the connector.

It is a further object of the present invention to provide a connector that allows for attachment to both the spinal rod and the implanted bone screw with only one locking mechanism.

It is another object of the present invention to provide a connector that provides for variable lateral distances between the spinal rod and the implanted pedicle screw.

SUMMARY OF THE INVENTION

The present invention is directed to a one piece connector for connecting angularly misaligned implanted pedicle screws to longitudinal spinal rods in spinal fixation systems. The one piece connector has a body portion and a leg portion that intersects the body portion at a 90° angle. The body portion includes a bore having an inside diameter and a longitudinal axis, with the longitudinal axis of the bore being positioned perpendicular to the longitudinal axis of the leg portion. The leg portion includes a slot placed through a section of the leg portion, the slot being placed along the transverse axis of the leg portion and parallel to the longitudinal axis of the leg portion. The slot intersects the bore of the body portion perpendicular to the longitudinal axis of the bore. The slot allows the one piece connector to be securely clamped around a longitudinal spinal rod when a pedicle screw is implanted at variable distances from the longitudinal spinal rod. The one piece connector allows for angular misalignment of an implanted pedicle screw in relation to a longitudinal spinal rod and the one piece connector, and for the attachment of the one piece connector to both the longitudinal spinal rod and to the implanted pedicle screw with a single locking mechanism when the one piece connector is used in a spinal fixation system.

BRIEF DESCRIPTION OF THE DRAWINGS

A better understanding of the invention can be obtained when the detailed description of exemplary embodiments set forth below is reviewed in conjunction with the accompanying drawings, in which:

FIG. 1 is a schematic view of a human spine with an implanted spinal fixation system using the connectors of the present invention;

FIG. 2 is a perspective view of a section of a spinal fixation system illustrating the connector of the present invention attaching a pedicle screw to a spinal rod;

FIG. 3 is a top plane view of the assembly of FIG. 2;

FIG. 4 is a perspective view of one embodiment of the present invention;

FIG. 5 is a perspective view of another embodiment of the present invention;

FIG. 6A is a cross-sectional view of the present invention of FIG. 4 taken along lines 6—6 showing the inner surface of the bore;

FIG. 6B is a cross-sectional view of the subject invention of FIG. 4 taken along lines 6—6 showing the bore tapering in a first direction;

FIG. 6C is a cross-sectional view of the present invention of FIG. 4 taken along lines 6—6 showing the inside surface of the bore tapering in a second direction;

FIG. 7 is a perspective view of the first end of the invention of FIG. 4;

FIG. 8 is a perspective of an alternative embodiment of the present invention;

FIG. 9 is a perspective view of a second alternative embodiment of the present invention;

FIG. 10 is a perspective view of a portion of the pedicle screw of FIG. 2 showing a locking mechanism for connecting the present invention to the implanted pedicle screw;

FIG. 11 is a plane view of the present invention of FIG. 2 illustrating a first range of rotation; and FIG. 12 is a side plane view of the present invention of FIG. 2 illustrating a second range of rotation.

DETAILED DESCRIPTION OF INVENTION

The present invention is directed to a one piece connector 10 that is used in spinal fixation systems such as the one shown in FIG. 1. Spinal fixation systems typically include spinal rods 12 and pedicle screws 42 or bone bolts (not shown). The one piece connector 10 includes a body portion 14 and a leg portion 16 (FIGS. 4 and 7). Body portion 14, in a preferred embodiment is generally cylindrical in shape with a longitudinal through bore 18 that has a longitudinal axis LA1—LA1, as shown in FIG. 5. However, body portion 14 can also have other shapes, such as for example, a spherical, oval or cubic shape. Bore 18 has a first end 20 and a second end 22 and an inside diameter D1—D1 (FIG. 6A) that in one embodiment is a constant dimension along the longitudinal axis LA1—LA1 from first end 20 to second end 22. Alternatively bore 18 can taper from a smaller inside diameter at first end 20 to a larger inside diameter D2—D2 at end 22 as shown in FIG. 6B or conversely bore 18 can taper from a larger diameter at end 20 to a smaller inside diameter D3—D3 at second end 22 as illustrated in FIG. 6C. However, in all embodiments, the inside diameter of bore 18 will be greater than an outside diameter of an appropriately sized spinal rod that is part of a spinal fixation system.

Leg portion 16 is generally a solid cylinder with a first end 24 and a second end 26 with the second end 26 intersecting the body portion 14 at a 90° angle (FIG. 7). Leg portion's 16 outer surface can be either smooth or textured. Leg portion 16 has a longitudinal axis LA2—LA2 (FIG. 5) and a transverse axis TA—TA (FIG. 7). Thus, longitudinal axis LA1—LA1 of bore 18 is positioned perpendicular to the longitudinal axis LA2—LA2 of leg portion 16. Leg portion 16 is split in two portions with a narrow slot 28, that is positioned along a transverse axis TA—TA and runs parallel to the longitudinal axis LA2—LA2 of leg portion 16 (FIGS. 4 and 7). Slot 28 includes a first end 30 and a second end 32 with first end 30 intersecting bore 18 of body portion 14 perpendicular to the longitudinal axis LA1—LA1 of bore 18, at the second end 26 of leg portion 16. Slot 28 has a constant width from first end 30 to second end 32 with the width being greater than the difference between the inside diameter of bore 18 and an outside diameter of a selected spinal rod 12. The width of slot 28 creates a clamping force on spinal rod 12 when the one piece connector 10 is placed over spinal rod 12 and connected to an implanted pedicle screw 42. Alternatively, the width of slot 28 can taper from a smaller width at first end 30 to a larger width at second end 32 or conversely from a larger width at first end 30 to a smaller width at second end 32. This tapering of the width of slot 28 increases the clamping force of the one piece connector 10 on spinal rod 12 when pedicle screw 42 is connected to the one piece connector 10 at variable points along the longitudinal axis LA2—LA2 of the leg portion 16. In one embodiment, second end 32 of slot 28 of the one piece connector 10 extends to and creates an opening in the first end 24 of leg portion 16 (FIGS. 4 and 7). In a second embodiment, as shown in FIG. 5, second end 32 of slot 28 stops short of the first end 24 of leg portion 16 so as to create a solid portion at the first end 24 of leg portion 16.

Alternatively, leg portion 16 of the one piece connector can taper from a larger outside diameter at second end 26 to a smaller outside diameter at first end 24 (FIG. 8) or conversely from a larger outside diameter at first end 24 to a smaller outside diameter at second end 26 of leg portion 16 (FIG. 9). The tapering of leg portion 16 also increases the clamping force of the one piece connector 10 on the longitudinal spinal rod 12 when pedicle screw 42 is connected to the one piece connector 10 at variable points along the longitudinal axis LA2—LA2 of the leg portion 16.

As an example only, one size of the one piece connector 10 can have a leg portion 16 with a length of approximately 0.49 inches and a diameter of approximately 0.2 inches, and a body portion 14 with an outside diameter of approximately 0.3 inches and a bore 18 with a diameter of approximately 0.2 inches.

The inside diameter of bore 18 of body portion 14 allows the one piece connector 10 to slide along the longitudinal spinal rod (line L—L in FIG. 3) in order to correctly position the one piece connector in relation to the implanted pedicle screw 42. The inside diameter of bore 18 of body portion 14 also allows for a 360° rotation of the one piece connector 10 around the spinal rod 12 (line T1—T1 in FIG. 11). This rotation allows for any transverse angular misalignment between the implanted pedicle screw 42 and the spinal rod 12 when the one piece connector is secured in place. The ability of the one piece connector to compensate for this angular misalignment reduces stress on the pedicle screw 42 and reduces lateral bending of the spinal rod 12 when the pedicle screw 42 is firmly fastened to the one piece connector 10 and the connector 10 is firmly clamped to spinal rod 12. Additionally, when the one piece connector 10 is attached to the pedicle screw 42, the generally circular shape of leg portion 16 allows the pedicle screw 42 to rotate 360° around leg portion 16 prior to being mechanically locked to the one piece connector 10 (line T2—T2 in FIG. 12). This rotation allows for any transverse angular misalignment between the one piece connector 10 and the implanted pedicle screw 42 when the one piece connector is secured in place. The ability of the one piece connector 10 to compensate for this angular misalignment also reduces stress on the pedicle screw 42 and reduces lateral bending of the spinal rod 12 when the pedicle screw 42 is firmly fastened to the one piece connector 10 and the connector 10 is firmly clamped to spinal rod 12.

The one piece connector 10 also allows the pedicle screw 42 to be offset at variable lateral distances from the spinal rod 12, as shown by line V-V in FIG. 3. The pedicle screw 42 can be locked to the one piece connector 10 at various selected points between the first and second ends 24, 26 of leg portion 16 of the one piece connector 10.

An inventive feature of the one piece connector 10 is its ability to be locked in place on both the longitudinal spinal rod 12 and the implanted pedicle screw 42 with a single locking mechanism on the pedicle screw 42. When used in a spinal fixation system, body portion 14 clamps around spinal rod 12. Pedicle screw 42 typically includes a U-shaped opening, a through bore or some other opening shaped to accommodate the one piece connector 10. Pedicle screw 42 including some form of a locking mechanism for locking the one piece connector 10 or other cylindrical member into the pedicle screw 42. Typical locking mechanisms found on pedicle screws or bone bolts include various kinds of tops or caps that include set screws or taper locking caps or a locking nut for use with bone bolts. These various locking mechanisms are known to one skilled in the art.

An example of a pedicle screw that can be used with the one piece connector is illustrated in FIGS. 2 and 10. Pedicle screw 42 has a shaft portion 44 and a top portion 46 that includes a U-shaped opening 48 configured to receive the one piece connector 10. As best seen in FIG. 10, the U-shaped opening 48 is defined by pair of opposed side walls and a floor. Each of the side walls has a tapered engagement slot formed therein for accommodating locking cap 50 and the floor has a hemi-cylindrical seat formed therein for accommodating the leg portion 16 of connector 10. Locking cap 50 has a pair of opposed tapered retention members for engaging the tapered engagement slots in the side walls of opening 48 and a hemi-cylindrical recess in a bottom surface thereof for accommodating the leg portion 16 of connector 10, In addition, a pair of supplemental retention members project outwardly from the top portion of locking cap 50 spaced from the tapered retention members. A locking cap 50 is inserted into the U-shaped opening 48 in order to clamp the one piece connector 10 into the pedicle screw 42. When the one piece connectors 10 are used in a spinal fixation system, the spinal rod 12 is placed through bore 18 of the body portion 14 of each connector and the connectors 10 are positioned along the spinal rod 12 in proper alignment with the implanted pedicle screws 42. The one piece connector 10 is angularly adjusted in order to compensate for the pedicle screws 42 that are misaligned in relation to the spinal rod 12. Head 46 of the pedicle screw 42 is positioned so that the U-shaped opening 48 is perpendicular to the longitudinal spinal rod 12. Leg portion 16 of the one piece connector 10 is placed through the U-shaped opening 48 and locking cap 50 is inserted into the U-shaped opening 48 in order to clamp the one piece connector 10 into the pedicle screw 42. As locking cap 50 is locked into place, it compresses the leg portion 16, which causes slot 28 to be compressed which causes body portion 14 of the one piece connector 10 to clamp around the spinal rod 12.

The one piece connector 10, thus provides a secure link between the spinal rod 12 and the implanted pedicle screw 42 with a single connector and a single locking mechanism. The one piece connector 10 allows the pedicle screw 44 to be clamped to the one piece connector at various angles and the one piece connector 10 to be clamped to the spinal rod 12 at various angles.

The foregoing disclosure and description of the invention are illustrative and explanatory thereof, and various changes in the details of the illustrated apparatus and construction and method of operation may be made without departing from the spirit of the invention.

What is claimed is:

1. A connector for connecting a bone fastener to an elongated spinal rod comprising:

a body portion having a longitudinal bore extending therethrough to receive an elongated spinal rod; and an elongated compressible leg portion extending from the body portion along an axis extending perpendicular to the longitudinal bore, the leg portion being configured and having a sufficient length to mount a bone fastener at variable longitudinal and angular positions along the length thereof.

2. A connector as recited in claim 1, wherein the leg portion is generally cylindrical in configuration.

3. A connector as recited in claim 2, wherein the leg portion is bifurcated along the longitudinal axis thereof to define two compressible hemi-cylindrical leg portions.

4. A connector as recited in claim 1, further comprising a bone fastener wherein the bone fastener has a top portion having a transverse bore extending therethrough and a bottom portion for engaging bone.

5. A connector as recited in claim 4, wherein the leg portion includes a transverse slot having a first end intersecting the longitudinal bore in the body portion to define a pair of leg members, the leg portion having a first diameter when the leg members are spaced from the transverse bore in the bone fastener and a second diameter when the leg members extend through the transverse bore, the second diameter being less than the first diameter.

6. A connector as recited in claim 1, wherein the leg portion includes a transverse slot having a first end intersecting the longitudinal bore in the body portion to define a pair of leg members and the transverse slot has a second end adjacent a distal end of the leg portion.

7. A connector as recited in claim 1, wherein the leg portion includes a transverse slot having a first end intersecting the longitudinal bore in the body portion to define a pair of leg members, and the transverse slot has a second end extending through a distal end of the leg portion.

8. A bone fastener in combination with a connector for securement of the bone fastener at a location offset from the axis of an elongated spinal rod comprising:

a) a connector having a first section configured to receive a spinal rod and having a second section defined by an elongated member extending perpendicular to the first section and having a longitudinal axis extending therethrough; and b) a bone fastener including:

i) a first portion having a transverse bore extending therethrough to receive the elongated member extending transversely from the spinal rod;

ii) a second portion depending from the first portion of the bone fastener and configured to secure the bone fastener to bone; and iii) locking member configured to engage the transverse bore of the first portion along the longitudinal axis of the elongated member and fix the position of the bone fastener with respect to the elongated member at a location offset from the axis of the spinal rod.

9. A bone fastener as recited in claim 8, wherein the second portion includes bone threads.

10. A bone fastener as recited in claim 8, wherein the elongated member is cylindrical in configuration.

11. A bone fastener as recited in claim 10, wherein the transverse bore in the first portion of the bone fastener is defined by a U-shaped opening having a pair of opposed side walls and a floor, each side wall having a tapered engagement slot formed therein, the floor having a hemi-cylindrical seat defined therein for accommodating a lower portion of the elongated member.

12. A bone fastener as recited in claim 11, wherein the locking member includes a top portion and a bottom portion, the bottom portion having a pair of opposed tapered retention members for engaging the tapered engagement slots in the opposed side walls of the U-shaped opening, and a hemi-cylindrical recess in a bottom surface thereof for accommodating an upper portion of the elongated member.

13. A bone fastener as recited in claim 11, wherein the top portion of the locking member includes a pair of supplemental retention members spaced from the opposed tapered retention members.

14. A bone fastener comprising:
a first portion having a transverse bore extending therethrough to receive an elongated member, the transverse bore being defined by a pair of opposed side walls, each side wall having a tapered engagement slot formed therein;
a second portion depending from the first portion and configured to secure the fastener to bone; and
a locking member configured to engage the transverse bore and fix the position of the bone fastener with respect to the elongated member, the locking member having a pair of opposed tapered retention members for engaging the tapered engagement slots in the opposed side walls of the transverse bore and a pair of supplemental retention members spaced from the opposed tapered retention members.

15. A bone fastener as recited in claim 14, wherein the elongated member is cylindrical in configuration.

16. A bone fastener as recited in claim 15, wherein the transverse bore is further defined by a lower portion having a hemi-cylindrical seat defined therein for accommodating a lower portion of the elongated member.

17. A bone fastener as recited in claim 15, wherein the locking member includes a hemi-cylindrical recess in a bottom surface thereof for accommodating an upper portion of the elongated member.

18. A bone fastener as recited in claim 14, wherein the second portion includes bone threads.

19. A spinal fixation system comprising:
an elongated spinal rod;
a bone fastener having a top portion defining a transverse bore and an elongated threaded shaft portion depending from the top portion;
a connector having a body portion with a longitudinal bore extending therethrough to receive the elongated spinal rod, and a compressible leg portion extending from the body portion along an axis extending perpendicular to the longitudinal bore, the leg portion configured to extend through the transverse bore in the top portion of the bone fastener and having a cylindrical cross-section to facilitate relative rotation of the bone fastener and the leg portion about the perpendicular axis thereof; and
a locking member configured to engage the transverse bore and compress the leg portion so as to fix the position of the bone fastener with respect to the leg portion.

20. A spinal fixation system as recited in claim 19, wherein the leg portion has a transverse slot intersecting the longitudinal bore in the body portion to define a pair of compressible leg members.

21. A spinal fixation system as recited in claim 20, wherein the transverse slot in the leg portion has a second end adjacent a distal end of the leg portion.

22. A spinal fixation system as recited in claim 20, wherein the transverse slot in the leg portion has a second end extending through a distal end of the leg portion.

23. A spinal fixation system as recited in claim 20, wherein the transverse bore in the top portion of the bone fastener is defined by a U-shaped opening having a pair of opposed side walls and a floor, each side wall having a tapered engagement slot formed therein, the floor having a hemi-cylindrical seat defined therein for accommodating a lower leg member of the leg portion.

24. A spinal fixation system as recited in claim 23, wherein the locking member includes a top portion and a bottom portion, the bottom portion having a pair of opposed tapered retention members for engaging the tapered engagement slots in the opposed side walls of the U-shaped opening, and a hemi-cylindrical recess in a bottom surface thereof for accommodating an upper leg member of the leg portion.

25. A spinal fixation system as recited in claim 24, wherein the top portion of the locking member includes a pair of supplemental retention members spaced from the opposed tapered retention members.

26. A spinal fixation system comprising:
a connector including a first portion having a first opening configured to slidably and rotatably receive an elongated spinal rod, and a second portion extending from the first portion and configured to mount a bone fastener; and
a single locking member configured to both fix the position of the first portion relative to the spinal rod and fix the position of the bone fastener relative to the second portion by engaging an outer circumferential surface of the second portion.

27. A spinal fixation system as recited in claims 26, further comprising a bone fastener having an opening defined therein for receiving the second portion of the connector.

28. A spinal fixation system as recited in claim 26, wherein the first portion defines a body portion having a longitudinal bore extending therethrough and the second portion defines a cylindrical leg portion extending from the body portion.

29. A spinal fixation system as recited in claim 28, wherein the leg portion has a transverse slot intersecting the longitudinal bore in the body portion to define a pair of compressible leg members such that the locking member effectuates compression of the body portion about the spinal rod as well as compression of the leg portion relative to the bone fastener.

30. A spinal fixation system as recited in claim 29, wherein the first opening is defined by a U-shaped opening having a pair of opposed side walls and a floor, each side wall having a tapered engagement slot formed therein, the floor having a hemi-cylindrical seat defined therein for accommodating a lower portion of the leg portion.

31. A spinal fixation system as recited in claim 30, wherein the locking member includes a top portion and a bottom portion, the bottom portion having a pair of opposed tapered retention members for engaging the tapered engagement slots in the opposed side walls of the U-shaped opening, and a hemi-cylindrical recess in a bottom surface thereof for accommodating an upper portion of the leg portion.

32. A spinal fixation system as recited in claim 31, wherein the top portion of the locking member includes a pair of supplemental retention members spaced from the opposed tapered retention members.

33. A connector for a spinal fixation system comprising:
a first portion having an opening to receive and substantially encircle an elongated spinal rod, the opening configured to facilitate rotation of the connector about the longitudinal axis of the spinal rod and facilitate longitudinal movement of the connector along the longitudinal axis of the spinal rod; and an elongated second portion extending from the first portion and defining a longitudinal axis extending transverse to the longitudinal axis of the spinal rod, the second portion being of a sufficient length and configuration to mount a bone fastener at various locations along the longitudinal axis thereof and at various angles about the longitudinal axis thereof.

34. A connector as recited in claim 33, further comprising a bone fastener, wherein the bone fastener has a top portion having a transverse bore therein for receiving the second portion of the connector and a bottom portion for engaging bone.

35. A connector as recited in claim 34, wherein the second portion defines a cylindrical leg portion having a transverse slot with a first end intersecting the opening in the first portion to define a pair of leg members.

36. A connector as recited in claim 35, wherein the transverse bore of the bone fastener is defined at least in part by a pair of opposed side walls each having a tapered engagement slot formed therein.

37. A connector as recited in claim 36, further comprising a locking member having a pair of opposed tapered retention members for engaging the tapered engagement slots in the opposed side walls of the transverse bore.

38. A connector for connecting a bone fastener to an elongated spinal rod comprising:

a body portion having a longitudinal bore extending therethrough to receive an elongated spinal rod; and a compressible leg portion extending from the body portion along an axis extending perpendicular to the longitudinal bore, the leg portion having a uniform outer surface along its length and being dimensioned and configured to mount a bone fastener and facilitate relative rotation of the fastener and the leg portion about a longitudinal axis thereof, wherein the leg portion is generally cylindrical in configuration and is bifurcated along the longitudinal axis thereof to define two compressible hemi-cylindrical leg portions.

39. A spinal fixation system comprising:
a) an elongated spinal rod;
b) a bone fastener having a top portion defining a transverse bore and an elongated threaded shaft portion depending from the top portion;
c) a connector having a body portion with a longitudinal bore extending therethrough to receive the elongated spinal rod, and a compressible leg portion extending from the body portion along an axis extending perpendicular to the longitudinal bore, the leg portion having a transverse slot intersecting the longitudinal bore in the body portion to define a pair of compressible leg members, the leg portion configured to extend through the transverse bore in the top portion of the bone fastener and having a cylindrical cross-section to facilitate relative rotation of the bone fastener and the leg portion about the perpendicular axis thereof; and
d) a locking member configured to engage the transverse bore and compress the leg portion so as to fix the position of the bone fastener with respect to the leg portion.

40. A spinal fixation system comprising:
a) a connector including a first portion having a first opening configured to slidably and rotatably receive an elongated spinal rod, and a second portion extending from the first portion and configured to mount a bone fastener;
b) a single locking member configured to both fix the position of the first portion of the connector relative to the spinal rod and fix the position of the bone fastener relative to the second portion of the connector; and
c) a bone fastener having an opening defined therein for receiving the second portion of the connector and the single locking member so as to facilitate fixation of the first portion of the connector relative to the spinal rod and fixation of the bone fastener relative to the second portion of the connector.

* * * * *